United States Patent [19]

Ward

[11] 4,225,613
[45] Sep. 30, 1980

[54] 1H-PYRROLE-1-ACETAMIDE COMPOUNDS AND THEIR PHARMACEUTICAL COMPOSITIONS

[75] Inventor: Terence J. Ward, Slough, England

[73] Assignee: John Wyeth & Brother Limited, Maidenhead, England

[21] Appl. No.: 35,026

[22] Filed: Apr. 30, 1979

[30] Foreign Application Priority Data

May 20, 1978 [GB] United Kingdom ............... 20986/78

[51] Int. Cl.$^2$ ..................... A61K 31/40; C07D 207/30
[52] U.S. Cl. ............................. 424/274; 260/326.25; 260/326.43
[58] Field of Search ....................... 260/326.25, 326.43; 424/274

[56] References Cited

U.S. PATENT DOCUMENTS 4,140,793   2/1979   Ward .................................... 424/224

Primary Examiner—Donald G. Daus
Assistant Examiner—Lisa Jones
Attorney, Agent, or Firm—Arthur E. Wilfond

[57] ABSTRACT

Pyrrole derivatives of general formula (II)

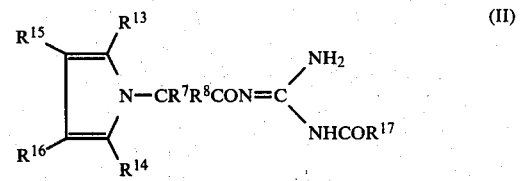

wherein $R^7$ and $R^8$ are the same or different and each represent hydrogen or lower alkyl, $R^{13}$ and $R^{14}$ are each hydrogen, lower alkyl or halogen with the proviso that at least one or $R^{13}$ and $R^{14}$ is halogen or (lower)alkyl, $R^{15}$ and $R^{16}$ are each hydrogen or lower alkyl and $R^{17}$ is aryl or aryl(lower)alkyl are useful as hypotensive or antihypertensive agents.

8 Claims, No Drawings

1H-PYRROLE-1-ACETAMIDE COMPOUNDS AND THEIR PHARMACEUTICAL COMPOSITIONS

This invention relates to novel pyrrole derivatives, to processes for their preparation and to pharmaceutical compositions containing them.

My U.S. Pat. No. 4,140,793 (published Feb. 20, 1979) discloses guanidine derivatives of the general formula (I)

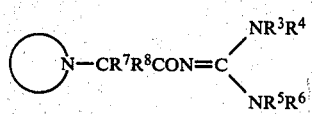

or pharmaceutically acceptable acid addition salts thereof, where

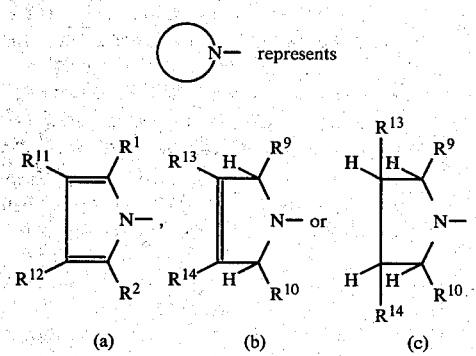

wherein $R^1$ and $R^2$ which may be the same or different each represent hydrogen, lower alkyl, trifluoromethyl or halogen and $R^{11}$ and $R^{12}$ which may be the same or different each represent hydrogen, lower alkyl, trifluoromethyl or halogen with the proviso that when one or both $R^{11}$ and $R^{12}$ groups represent halogen then $R^1$ and $R^2$ each represent lower alkyl, trifluoromethyl or halogen, $R^9$ and $R^{10}$ which may be the same or different each represent hydrogen, lower alkyl or trifluoromethyl and $R^{13}$ and $R^{14}$ which may be the same or different each represents hydrogen, lower alkyl, trifluoromethyl or halogen with the proviso that when one or both $R^{13}$ and $R^{14}$ groups represent halogen then $R^9$ and $R^{10}$ each represent lower alkyl or trifluoromethyl and $R^7$ and $R^8$ are the same or different and each represent hydrogen or lower alkyl and $R^3$, $R^4$, $R^5$ and $R^6$ are the same or different and each represent hydrogen or lower alkyl or $R^4$ and $R^6$ are each hydrogen and $R^3$ and $R^5$ together represent dimethylene or trimethylene such that

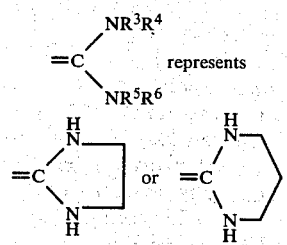

The present invention provides novel pyrrole derivatives of the general formula (II)

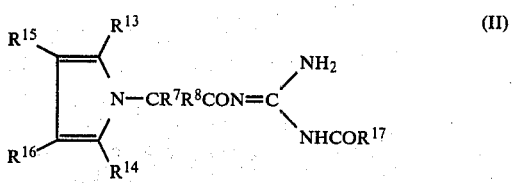

wherein $R^7$ and $R^8$ and as defined above, $R^{13}$ and $R^{14}$ are each hydrogen, lower alkyl or halogen with the proviso that at least one of $R^{13}$ and $R^{14}$ is halogen or (lower)alkyl, $R^{15}$ and $R^{16}$ are each hydrogen or lower alkyl and $R^{17}$ is aryl or aryl(lower)alkyl.

The term "lower" as used herein means that the radical referred to contains from 1 to 6 carbon atoms. Preferably the radical contains from 1 to 4 carbon atoms.

When $R^7$ or $R^8$ is lower alkyl it can be, for example, methyl, ethyl, propyl or butyl. Preferably both $R^7$ and $R^8$ are hydrogen.

$R^{13}$ and $R^{14}$ can be hydrogen, lower alkyl (e.g. methyl, ethyl, propyl or butyl) or halogen (e.g. fluorine, chlorine or bromine) provided that both $R^{13}$ and $R^{14}$ are both not hydrogen. Preferably both $R^{13}$ and $R^{14}$ are chlorine.

$R^{15}$ and $R^{16}$ can be the same or different. Example of lower alkyl groups for $R^{15}$ and $R^{16}$ are methyl, ethyl, propyl or butyl. Preferably both $R^{15}$ and $R^{16}$ are hydrogen.

When $R^{17}$ is aryl it is preferably phenyl or substituted phenyl. The phenyl group may be substituted by, for example, one or more of the substituents common in medicinal chemistry such as lower alkyl (e.g. methyl, ethyl, propyl or butyl), lower alkoxy (e.g. methoxy, ethoxy, propyloxy, butyloxy), halogen (e.g. fluorine, chlorine or bromine) and trifluoromethyl. When $R^{17}$ is aryl(lower)alkyl the aryl group is preferably phenyl or substituted phenyl (where the substituents can be, for example, those mentioned immediately above). Thus the $R^{17}$ group can be, for example, benzyl, substituted benzyl, phenethyl (where the phenyl group may optionally be substituted) and the like. The term "aryl" includes heterocyclic radicals having aromatic character and, for example, $R^{17}$ can be a radical of the formula

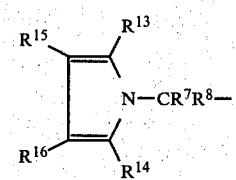

where $R^7$, $R^8$, $R^{13}$, $R^{14}$, $R^{15}$ and $R^{16}$ have the meanings given above.

The compounds of the invention of general formula (II) may be prepared by acylating a guanidine derivative of general formula (III)

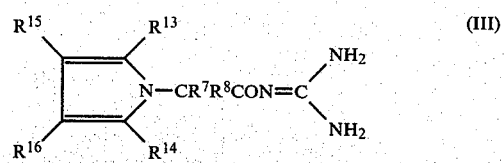

(where $R^7$, $R^8$, $R^{13}$, $R^{14}$, $R^{15}$ and $R^{16}$ have the meanings given above) with an acylating derivative of an acid of general formula (IV)

 (IV)

(where $R^{17}$ has the meaning given above) or, alternatively, by acylating a guanidine derivative of general formula (V)

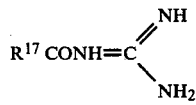 (V)

(where $R^{17}$ has the meaning given above) with an acylating derivative of an acid of general formula (VI)

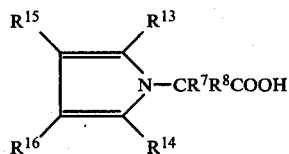 (VI)

(where $R^7$, $R^8$, $R^{13}$, $R^{14}$, $R^{15}$ and $R^{16}$ have the meanings given above). Preferably the acylating derivative is an acyl halide (e.g. an acyl chloride) or acyl anhydride of the acid.

The guanidine derivatives of general formula (III) are described in U.S. Pat. No. 4,140,793, mentioned above. The guanidine derivatives of general formula (V) may, for example, be prepared by reacting an acylating derivative of the acid of general formula (IV) with guanidine. Methods for preparing the acids of general formula (VI) and their acylating derivatives are described, for example, in our above mentioned complete specification.

The compounds of the invention are illustrated in formula (II) in a particular tautomeric form but it is possible that the compounds exist in other tautomeric forms or mixtures of such forms. For example possible structures of compounds in which $R^7$ and $R^8$ are hydrogen include:

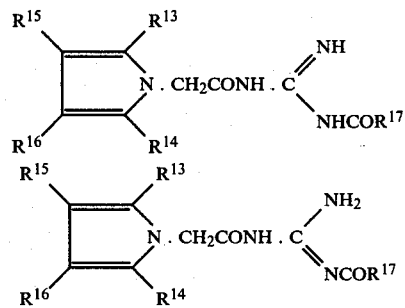

as well as enol forms such as

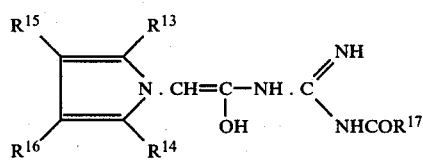

Where in this specification there is used a name or formula implying any particular tautomeric form it is to be understood that the name of formula includes any of the other alternative forms or a mixture of such forms.

The compounds of the invention lower blood pressure as indicated by standard hypotensive or antihypertensive pharmacological procedures. For example, N-[amino(benzoylamino)methylene]-2,5-dichloro-pyrrole-1-acetamide, a representative compound of the invention, showed antihypertensive at a dose of 50 mg/kg when administered orally to hypertensive rats. Some of the compounds, for example, 1,3-di[2,5-dichloro-1H-pyrrol-1-yl)acetyl]guanidine are also anti-ulcer agents which show antisecretory activity when tested by the procedure of Shay et al, Gastroenterology 1954, 26, 903-13.

The invention includes a pharmaceutical composition comprising a compound of general formula (II) in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance, aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage form can be a packaged composition the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 mg or more, according to the particular need of the patient and the activity of the active ingredient. The invention also includes the compounds in the absence of the carrier where the compounds are in unit dosage form.

The following Examples illustrate the invention.

EXAMPLE 1

N-[Amino(benzoylamino)methylene]-2,5-dichloro-1H-pyrrole-1-acetamide

Benzoyl chloride (0.77 g.) was added dropwise to a stirred ice cooled solution of N-diaminomethylene-2,5-dichloro-1H-pyrroleacetamide (1.16 g.) in hexamethylphosphoramide (5 cm³). After ½ hour a further aliquot of benzoyl chloride (0.3 g) was added and the reaction stirred at room temperature for ½ hour then poured into water and the precipitate extracted into chloroform, washed with sodium carbonate solution, dried, and evaporated. The residue was triturated with ethanol (20 cm³) and the crystalline product collected by filtration to give the title compound (0.7 g.) m.p. 212°–213° C.

EXAMPLE 2

N-[Amino[(4-Chlorobenzoyl)amino]methylene]-2,5-dichloro-1H-pyrrole-1-acetamide p-Chlorobenzoyl chloride (1.05 g) was added rapidly to a stirred solution of N-diaminomethylene-2,5-dichloro-1H-pyrroleacetamide (1.16 g.) in dry pyridine (5 cm³.). The solution was allowed to stand for 1 hour and diluted with water. The precipitated product was collected by filtration, washed with water, and crystallised four times from acetonitrile and twice from ethanol to give the title compound (0.45 g.) m.p. 198°–200° C.

EXAMPLE 3

N-[Amino[(4-methoxybenzoyl)amino]methylene]-2,5-dichloro-1H-pyrrole-1-acetamide p-Methoxybenzoyl chloride (1.02 g.) was added rapidly to a stirred solution of N-diaminomethylene-2,5-dichloro-1H-pyrroleacetamide (1.16 g.) in dry pyridine (5 cm³). After standing for 1 hour the mixture was diluted with water and the precipitated solid collected by filtration, washed with water, and crystallised thrice from acetonitrile to give the title compound (0.68 g.) m.p. 215°–17° C.

EXAMPLE 4

N-[Amino(phenylacetamido)methylene]-2,5-dichloro-1H-pyrrole-1-acetamide

Phenylacetyl chloride (0.8 cm³, 0.925 g.) was added rapidly to a stirred solution of N-diaminomethylene-2,5-dichloro-1H-pyrroleacetamide (1.16 g.) in dry pyridine (5 cm³). The solution was allowed to stand for 1 hour and then diluted with water, acidified by addition of hydrochloric acid and ether (10 cm³) added. On stirring in ice the crystalline product separated and was collected by filtration and crystallised from ethanol to give the title compound (0.5 g.) m.p. 181°–3° C.

EXAMPLE 5

1,3-Di[2,5-dichloro-1H-pyrrol-1-yl)acetyl]guanidine (2,5-Dichloro-1H-pyrrol-1-yl)acetyl chloride (2.5 g.) was added rapidly to a stirring solution of N-diaminomethylene-2,5-dichloro-1H-pyrroleacetamide (2.36 g.) in pyridine (10 cm³, dried over KOH). The solution was stirred for a further 0.5 hours and water (40 cm³) was added. The solution was cooled and the precipitated solid filtered off. The solid was dried and recrystallised from ethanol to give the title compound (0.95 g.) m.p. 196°–198° C.

I claim:

1. A pyrrole or the formula

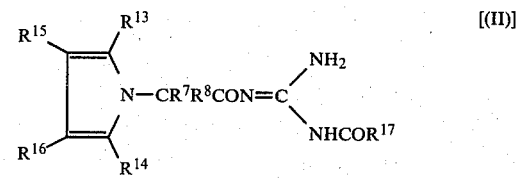

wherein $R^7$ and $R^8$ are the same or different and each represent hydrogen or lower alkyl, $R^{13}$ and $R^{14}$ are each hydrogen, lower alkyl or halogen with the proviso that at least one of $R^{13}$ and $R^{14}$ is halogen or (lower) alkyl, $R^{15}$ and $R^{16}$ is halogen or (lower) alkyl, $R^{17}$ is phenyl, substituted phenyl, phenyl (lower) alkyl, substituted phenyl (lower) alkyl, wherein the substituted phenyl radical is phenyl substituted by one or more unhindered substituents selected from the group consisting of lower alkyl, lower alkoxy, halogen and trifluoromethyl substituents; or a radical of the formula

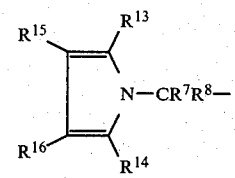

where $R^7$, $R^8$, $R^{13}$, $R^{14}$, $R^{15}$ and $R^{16}$ have the meanings above.

2. A compound of claim 1 which is N-[amino(benzoylamino) methylene]-2,5-dichloro-1H-pyrrole-1-acetamide.

3. A compound of claim 1 which is N-[amino[(4-chlorobenzoyl) amino]methylene]-2,5-dichloro-1H-pyrrole-1-acetamide.

4. A compound of claim 1 which is N-[amino[(4-methoxybenzoyl) amino]methylene]-2,5-dichloro-1H-pyrrole-1-acetamide.

5. A compound of claim 1 which is N-[amino(-phenylacetamido) methylene]-2,5-dichloro-1H-pyrrole-1-acetamide.

6. A compound of claim 1 which is 1,3-di[2,5-dichloro-1H-pyrrol-1-yl)acetyl]guanidine.

7. A pyrrole as claimed in claim 1 wherein $R^7$, $R^8$, $R^{15}$ and $R^{16}$ are each hydrogen and $R^{13}$ and $R^{14}$ are both chlorine.

8. A pharmaceutical composition having hypotensive or antihypertensive activity comprising a pyrrole of the formula

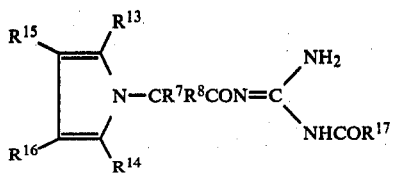

wherein $R^7$ and $R^8$ are the same or different and each represent hydrogen or lower alkyl, $R^{13}$ and $R^{14}$ are each hydrogen, lower alkyl or halogen with the proviso that at least one $R^{13}$ and $R^{14}$ is halogen or alkyl, $R^{15}$ and $R^{16}$ are each hydrogen or lower alkyl and $R^{17}$ is phenyl, substituted phenyl, phenyl (lower) alkyl, substituted phenyl (lower) alkyl, wherein the substituted phenyl radical is phenyl substituted by one or more lower alkyl, lower alkoxy, halogen or trifluoromethyl substituents; or a radical of the formula

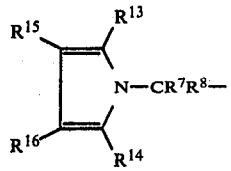

wherein $R^7$, $R^8$, $R^{13}$, $R^{14}$, $R^{15}$, and $R^{16}$ have the meanings above in association with a pharmaceutically acceptable carrier.

* * * * *